US009927442B1

(12) United States Patent
Klein et al.

(10) Patent No.: US 9,927,442 B1
(45) Date of Patent: *Mar. 27, 2018

(54) BIOSENSOR FOR IN VITRO DETECTION SYSTEM AND METHOD OF USE

(71) Applicant: Verily Life Sciences LLC, Mountain View, CA (US)

(72) Inventors: Joshua Simon Klein, Mountain View, CA (US); Vikram Singh Bajaj, Mountain View, CA (US); Victor Marcel Acosta, San Francisco, CA (US); Jerrod Joseph Schwartz, San Francisco, CA (US); Jason Donald Thompson, Palo Alto, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 177 days.

This patent is subject to a terminal disclaimer.

(21) Appl. No.: 14/580,644

(22) Filed: Dec. 23, 2014

Related U.S. Application Data

(60) Provisional application No. 62/073,759, filed on Oct. 31, 2014.

(51) Int. Cl.
*G01N 33/543* (2006.01)
*G01N 33/68* (2006.01)

(52) U.S. Cl.
CPC ... *G01N 33/6845* (2013.01); *G01N 33/54306* (2013.01); *G01N 33/54386* (2013.01); *G01N 2458/00* (2013.01)

(58) Field of Classification Search
CPC ......... G01N 33/6845; G01N 33/54306; G01N 33/54386
See application file for complete search history.

(56) References Cited

U.S. PATENT DOCUMENTS

| | | | |
|---|---|---|---|
| 4,469,787 A * | 9/1984 | Woods | G01N 33/54306 422/400 |
| 4,640,898 A | 2/1987 | Halfman | |
| 5,545,806 A | 8/1996 | Lonberg et al. | |
| 5,569,825 A | 10/1996 | Lonberg et al. | |
| 5,625,126 A | 4/1997 | Lonberg et al. | |
| 6,166,125 A | 12/2000 | Sugiyama et al. | |
| 6,590,036 B2 | 7/2003 | Koike et al. | |
| 6,593,415 B2 | 7/2003 | Koike et al. | |
| 6,653,425 B1 | 11/2003 | Armstrong-Poston et al. | |
| 7,491,552 B2 | 2/2009 | McDevitt et al. | |
| 7,906,280 B2 | 3/2011 | Bruno et al. | |
| 8,153,390 B2 | 4/2012 | Bradshaw et al. | |
| 8,574,925 B2 | 11/2013 | Jibu | |
| 8,715,951 B2 | 5/2014 | Parhami-Seren et al. | |
| 2003/0153013 A1 | 8/2003 | Huang | |
| 2005/0118619 A1 | 6/2005 | Xia et al. | |
| 2009/0186342 A1 | 7/2009 | Bruno et al. | |
| 2009/0227043 A1* | 9/2009 | Huang | G01N 33/582 436/501 |
| 2012/0094277 A1 | 4/2012 | Bruno et al. | |
| 2012/0219961 A1 | 8/2012 | Bruno et al. | |
| 2014/0005069 A1 | 1/2014 | Yang et al. | |
| 2014/0025000 A1 | 1/2014 | Currie et al. | |
| 2014/0038222 A1* | 2/2014 | Alt | G01N 21/63 435/29 |

FOREIGN PATENT DOCUMENTS

| | | | |
|---|---|---|---|
| WO | 2006107921 A2 | 10/2006 | |
| WO | 2009105583 A1 | 8/2009 | |
| WO | 2014014897 A2 | 1/2014 | |

OTHER PUBLICATIONS

Marianayagam et al., "The power of two: protein dimerization in biology," Trends Biochem. Sci., 2004, vol. 29, issue 11, pp. 618-625.*
Stringer et al., "Quantum Dot-Based Biosensor for Detection of Human Cardiac Troponin I Using a Liquid-Core Waveguide," IEEE Sensors, 2008, vol. 8, issue 3, pp. 295-300.*
Arruebo, et al., "Antibody-Conjugated Nanoparticles for Biomedical Applications", Journal of Nanomaterials, 2009, vol. 2009, Article ID 439389, 24 pages (available at http://dx.doi.org/10.1155/2009/439389).
Auld, et al., "Receptor Binding Assays for HTS and Drug Discovery", Assay Guidance Manual, May 1, 2012, pp. 1-33 (available at http://www.ncbi.nlm.nih.gov/books/NBK91992/).
Davenport, et al., "Radioligand Binding Assays: Theory and Practice", Current Directions in Radiopharmaceutical Research and Development, 1996, vol. 30, pp. 169-179.
Grover, et al., "A Structurally Distinct Human Mycoplasma Protein that Generically Blocks Antigen-Antibody Union", Science, Feb. 7, 2014, vol. 343, pp. 656-661.
Marras, "Selection of Fluorophore and Quencher Pairs for Fluorescent Nucleic Acid Hybridization Probes", Methods in Molecular Biology, 2006, vol. 335, pp. 3-16.
"Antibody", Wikipedia, pp. 1-22. [Retrieved from the Internet Sep. 8, 2014:<URL:http://en.wikipedia.org/wiki/Antibody>].
"Fluorescent Glucose Biosensor", Wikipedia, pp. 1-16. [Retrieved from the Internet Sep. 10, 2014:<URL:http://en.wikipedia.org/wiki/Fluorescent_glucose_biosensor>].
"Fluorescent Labelling", Wikipedia, pp. 1-2. [Retrieved from the Internet Sep. 8, 2014:<URL:http://en.wikipedia.org/wiki/Fluorescent_labelling>].
"Forster Resonance Energy Transfer", Wikipedia, pp. 1-11. [Retrieved from the Internet Jul. 29, 2014:<URL:http://en.wikipedia.org/wiki/Forster_resonance_energy_transfer>].

(Continued)

*Primary Examiner* — Galina Yakovleva
(74) *Attorney, Agent, or Firm* — McDonnell Boehnen Hulbert & Berghoff LLP (57) ABSTRACT

A device and system for detecting an antigen present in a sample is provided. The system includes a cartridge and a reader device. The cartridge includes a solid support having an addressable array of at least one type of antibody that is specific for a target antigen and forms a complex in the presence of the target antigen, a substrate having a mounting surface for the solid support, Protein M for competitively displacing the target antigen from the complex, and a housing for protecting the substrate. The reader device is configured to detect the antigen in a liquid sample via interaction with the cartridge.

11 Claims, 5 Drawing Sheets

(56) References Cited

OTHER PUBLICATIONS

"Real-Time PCR: Guidelines for Use of Fluorophores and Quenchers", Technical Bulletin 002-2011, Microsynth AG, pp. 1-2. (Abstract only).

Gold, et al, "Aptamer-Based Multiplexed Proteomic Technology for Biomarker Discovery", PLoS ONE, Dec. 2010, vol. 5(12), pp. 1-17.

Larson, "Hermes: Handheld Device Created to Isolate, Purify Biological Samples for Diagnosis", Nursezone.com, Jun. 14, 2002, pp. 1-2.

Pai, et al, "A Handheld Magnetic Sensing Platform for Antigen and Nucleic Acid Detection", Analyst, Dec. 10, 2013, vol. 139, pp. 1403-1411, doi:10.1039/C3AN01947K.

"Multiplexing DELFIA Assays Using Lanthanide-Labeled Probes", PerkinElmer Life Sciences, pp. 1-8. [Retrieved from the Internet Oct. 29, 2014:<URL:http://www.perkinelmer.com/lifesciences.html>].

"SOMAscan(TM) Proteomic Assay", SomaLogic, 2013, pp. 1-24.

"QuantuMDx is The Future", QuantuMDx, pp. 1-4. [Retrieved from the Internet Oct. 29, 2014:<URL:http://www.quantumdx.com/technology-overview.html>].

Borrebaeck, C.A.K., "Antibodies in Diagnostic—from Immunoassays to Protein Chips", Immunology Today, Aug. 1, 2000, vol. 21(8), pp. 379-382. (Abstract only).

Deng, Y., et al., "Preparation of Magnetic Polymeric Particles via Inverse Microemulsion Polymerization Process", Journal of Magnetism and Magnetic Materials, Feb. 2003, vol. 257(1), pp. 69-78. (Abstract only).

Fang, W., et al., "Superparamagnetic Core-shell Polymer Particles for Efficient Purification of His-tagged Proteins", Journal of Materials Chemistry, 2010, vol. 20, pp. 8624-8630, DOI:10.1039/C0JM02081H. (Abstract only).

Siddiqui, M.Z., et al., "Monoclonal Antibodies as Diagnostics; An Appraisal", Indian J. Pharm. Sci., Jan. 2010, vol. 72 (1), pp. 12-17, doi:10.4103/0250-474X.62229.

Richieri, Gary V., et al.,"A Flourescently Labeled Intestinal Fatty Acid Binding Protein", J. Biol. Chem., Nov. 25, 1992, vol. 267(33), pp. 23495-23501.

Alvarez, et al., "A Phase I Study of Recombinant Adenovirus Vector-Medicated Delivery of an Anti-erbB-2 Single-Chain (sFv) Antibody Gene for Previously Treated Ovarian and Extraovarian Cancer Patients," Hum. Gene Ther., Jan. 20, 1997, vol. 8, pp. 229-242. (Partial Abstract).

Held, "An Introduction to Fluorescence Resonance Energy Transfer (FRET) Technology and its Application in Bioscience", Jun. 20, 2005, pp. 1-10, from BioTek Catalog (available at http://www.biotek.com/resources/articles/fluorescence-resonance-energy-transfer.html).

* cited by examiner

BIOSENSOR FOR IN VITRO DETECTION SYSTEM AND METHOD OF USE

CROSS-REFERENCE

This application claims the benefit of priority from U.S. Provisional application Ser. No. 62/073,759, filed Oct. 31, 2014, which is incorporated by reference in its entirety.

BACKGROUND

Unless otherwise indicated herein, the materials described in this section are not prior art to the claims in this application and are not admitted to be prior art by inclusion in this section.

A number of scientific methods have been developed to detect and/or measure one or more antigens in a person's bodily fluids such as blood or saliva. The presence or absence of an antigen in the blood, or the presence at a particular concentration or range of concentrations, may be indicative of a medical condition or the person's state of health. Representative antigens may include enzymes, proteins, cells, viral or bacterial markers, or other molecules.

In a typical scenario, a person's bodily fluid, e.g., blood, is drawn and sent to a lab where a variety of diagnostic tests are performed to detect and measure various antigen levels and parameters in the blood. The variety of tests may be referred to as "blood work," where the blood is tested for the presence of various diseases, or antigen levels such as HIV viral load, etc. For most people, the blood tests are infrequent, and the present of an antigen or an abnormal antigen level indicative of a medical condition may not be identified for some time after the blood work is performed, which can lead to delayed treatment of a disease.

Rapid multiplexed diagnostic technologies have the potential to improve many areas of healthcare. Some examples include reducing the cost and time for diagnosis, increasing the specificity of diagnosis, monitoring patient response and adherence to therapy, increasing early detection of preventable disease, and rapidly assessing the prevalence of disease outbreaks outside of the laboratory or hospital. However, there are a number of disadvantages with the current diagnostic technologies, particularly those that rely on nucleic acid based technology such as slow-off rate aptamers which can be relatively difficult to engineer, sensitivity of aptamer affinity to minor perturbations in concentrations of solutes such as metal ions; and extensive sample preparation and restriction to detection of antigens that can be conjugated to biotin. Accordingly, there is a need for improved device, system, and method that overcomes such deficiencies.

SUMMARY

One aspect of the present disclosure provides a system. The system includes a cartridge device comprising: (a) a solid support having an addressable array of at least one type of antibody immobilized thereon, wherein each type of antibody is specific for a target antigen and forms a complex in the presence of the target antigen, and wherein each type of antibody has a detectable label that is different; Protein M for competitively displacement of the target antigen in the complex; a substrate having a mountable surface for the solid support; a protective housing for the substrate; and (b) a reader device, wherein the reader device is configured to detect the target antigen via interaction with the cartridge device.

In some embodiments, the substrate includes an antibody array configured to undergo an optically-detectable change upon interaction with a target antigen. The optically-detectable change may involve a change in at least one of optical absorption, reflectivity, or fluorescence. The substrate can be used in conjunction with a reader device configured to detect the optically-detectable change. The reader device may include an excitation light source configured to direct light toward the substrate, and a photodetector configured to detect light from the substrate. The detected optical change can be used to determine the presence/absence of an antigen or the concentration of an antigen. The system can be a portable, handheld device.

In another aspect, the present disclosure provides a system. The system includes: (a) a cartridge device comprising: a solid support having an addressable array of immobilized complexes of at least one type of antibody and Protein M, wherein each type of antibody is specific for a target antigen and wherein the Protein M and the at least one type of antibody have different detectable labels; a substrate having a mountable surface for the solid support; and a protective housing for the substrate; and (b) a reader device, wherein the reader device is configured to detect the target antigen via interaction with the cartridge.

In another aspect, the present disclosure provides a device. A device comprising: (a) a solid support; and (b) a plurality of complexes of at least one type of antibody and Protein M immobilized on the solid support in an addressable array, wherein each type of antibody is specific for a target antigen, wherein the Protein M and each type of antibody have detectable labels that are different. In some embodiments, Protein M is monomeric or dimeric. In other embodiments, the device further comprises a substrate having a mountable surface for mounting the solid support and a housing for protecting the substrate.

In another aspect, the present disclosure provides another device. The device includes: (a) a solid support having an addressable array of at least one type of antibody, each type of antibody having a detectable label that is different, wherein each type of antibody is immobilized onto the solid support, wherein each type of antibody is specific for a target antigen and forms a complex in the presence of the target antigen. (b) Protein M for competitive displacement of the target antigen from the complex; (c) a substrate having a mountable surface for the solid support; and (d) a protective housing for the substrate.

In another aspect, the present disclosure provides a further device. The device includes: (a) a solid support having an addressable array of immobilized complexes of at least one type of antibody and Protein M, wherein each type of antibody is specific for a target antigen, wherein the Protein M and each type of antibody have detectable labels that are different; (b) a substrate having a mountable surface for the solid support; and (c) a protective housing for the substrate.

In another aspect, the present disclosure provides yet a further device. The device includes: (a) a solid support; and (b) a plurality of complexes of at least one type of antibody and Protein M immobilized on the solid support in an addressable array, wherein each type of antibody is specific for a target antigen, wherein the Protein M and each type of antibody have detectable labels that are different. The Protein M can be monomeric or dimeric. In some embodiments, the device further includes a substrate having a mountable surface for mounting the solid support and housing for protecting the substrate.

In another aspect, the present disclosure provides a method. The method includes: (a) contacting a sample of biological fluid suspected of having one or more target antigens to a solid support having an addressable array of at least one type of antibody, wherein each type of antibody is immobilized to the solid support, wherein each type of antibody is specific for a target antigen and wherein each type of antibody has a detectable label that is different, and wherein the contacting occurs under conditions that allow for formation of a first complex of the one or more target antigens present in the biological fluid with the at least one type of antibody that is specific for the target antigen; (b) washing the solid support to remove uncomplexed target antigens; (c) contacting the solid support with Protein M under conditions that allow the labeled Protein M to bind to each type of antibody that is not complexed to form a second complex, wherein the Protein M has a detectable label that is different from the detectable label for each type of antibody; (d) washing the solid support to remove uncomplexed Protein M; and (e) determining the presence or absence of the one or more target antigens by transmitting incident light to the solid support and detecting light emitted by the antibodies, Protein M, or both.

In another aspect, the present disclosure provides yet another method. The method includes: (a) transmitting incident light from a reader device to a cartridge comprising a solid support mounted to a substrate, the solid support having an addressable array of immobilized first complexes of at least one type of antibody and a target antigen and immobilized second complexes of at least one type of antibody and Protein M, wherein each type of antibody is specific for a target antigen and wherein the Protein M and each type of antibody has detectable labels that are different; (b) receiving, by the reader device, fluorescence light emitted by the antibodies and Protein M; and (c) detecting the presence or absence of the one or more target antigens based on the fluorescence light received by the reader.

These as well as other aspects, advantages, and alternatives, will become apparent to those of ordinary skill in the art by reading the following detailed description, with reference where appropriate to the accompanying drawings.

DETAILED DESCRIPTION

I. Overview

The present disclosure relates to a device, system and method for the rapid, multiplexed, customizable detection of antigens for which an antibody exists or can be developed. Further, these approaches need not be limited by the antibody isotype or the species from which the antibody originated. The detection is based on the use of Protein M, a recently discovered protein isolated from mycoplasma that binds non-specifically to antibodies of multiple species and isotypes and blocks access to the antigen binding site. Protein M serves as a "universal" antigen for most, if not all, antibodies and competes with the targeted antigen for the antigen binding. When the targeted antigen is present in sufficient concentration in a liquid sample, the target antigen competitively displaces a portion of the Protein M molecule from the antigen binding site in antibody-Protein M complexes to form an antibody-targeted antigen-complex. In examples, the antibodies and Protein M are detectably labeled, such that ratiometric determinations from fluorescence emissions from the antibodies and Protein M complexed to the antibodies can be made to determine the presence and concentration of the target antigen in a sample.

Systems for monitoring antigen levels can include a cartridge device and a reader device. The cartridge device may include a solid support having an addressable array of at least one type of antibody, each type of antibody having a detectable label that is different, wherein each type of antibody is immobilized onto the solid support, wherein each type of antibody is specific for a target antigen and forms a complex in the presence of the target antigen, a substrate having a mountable surface for the solid support; and a protective housing for the substrate. The cartridge device includes Protein M which competes with the target antigen for the antigen binding site of the antibody. Protein M can be present as a reagent with the cartridge or as a complex with each type of antibody. The reader device can detect the antigen by optically interrogating the antibody array on the substrate. Alternatively or additionally, the cartridge device may include its own optical sensor, control electronics, and an antenna for wireless communication with the reader. The control electronics can operate the sensor to perform readings and can operate the antenna to wirelessly communicate the readings from the sensor to the reader device via the antenna. The cartridge device can include reagents such as Protein M and buffers as well as other components, e.g., microfluidic pumps and structures, to enable a biochemical reaction to occur.

A liquid sample, e.g., blood, urine, saliva, or sweat, taken from a person, can be added to the cartridge device, e.g., by injection, and the biochemical reaction occurs within the cartridge device. The cartridge device can include an array of antibodies of targeted specificities such an array of antibodies to specific HIV subtypes or to specific cancer biomarkers.

Bodily fluids contain a variety of antigens that can be used to diagnose health status and disease. Bodily fluids can also contain a variety of disease markers or agents such cancer markers, viral or bacterial markers that can be used to diagnose disease and health states. A system including the above-mentioned antibody array configured to measure one or more of these antigens can thus provide a convenient platform useful in diagnosing and/or monitoring health states. For example, a system can be configured to sense HIV virus and can be used by HIV infected individuals to measure/monitor their viral load levels.

After completion of biochemical reaction in the cartridge device, the cartridge device can be interrogated by a reader device.

An external reader device or "reader" can optically interrogate the cartridge device. For example, the reader can transmit incident light that excites a fluorophore in the antibody array and receive fluorescence light from the array interacting with the target antigen, Protein M, or both. The reader may detect the target antigen (and may determine the concentration of the target antigen in the liquid sample) based on the fluorescence light.

The antigen concentration information can be sent from the reader to a display device. In some embodiments, the reader is also the display device. In other embodiments, the display device could be, for example, a wearable, laptop, desktop, handheld, or tablet computer, a mobile phone, or a subsystem of such a device. The display device can include a processing system; e.g., a central processing unit (CPU), and a non-transitory computer readable medium configured to store at least program instructions. One example of a wearable computer is a head-mountable display (HMD). The HMD can be a device that is capable of being worn on the head and places a display in front of one or both eyes of the wearer. The display device can store the data received from the reader, perhaps process the data, and generate display(s) based on the received and/or processed data.

In some embodiments, the cartridge device can be insertable into the reader device to form a portable, handheld device. After the cartridge device is interrogated by the reader, the used cartridge device can be removed from the reader device and discarded.

II. Example System

Figure 1:
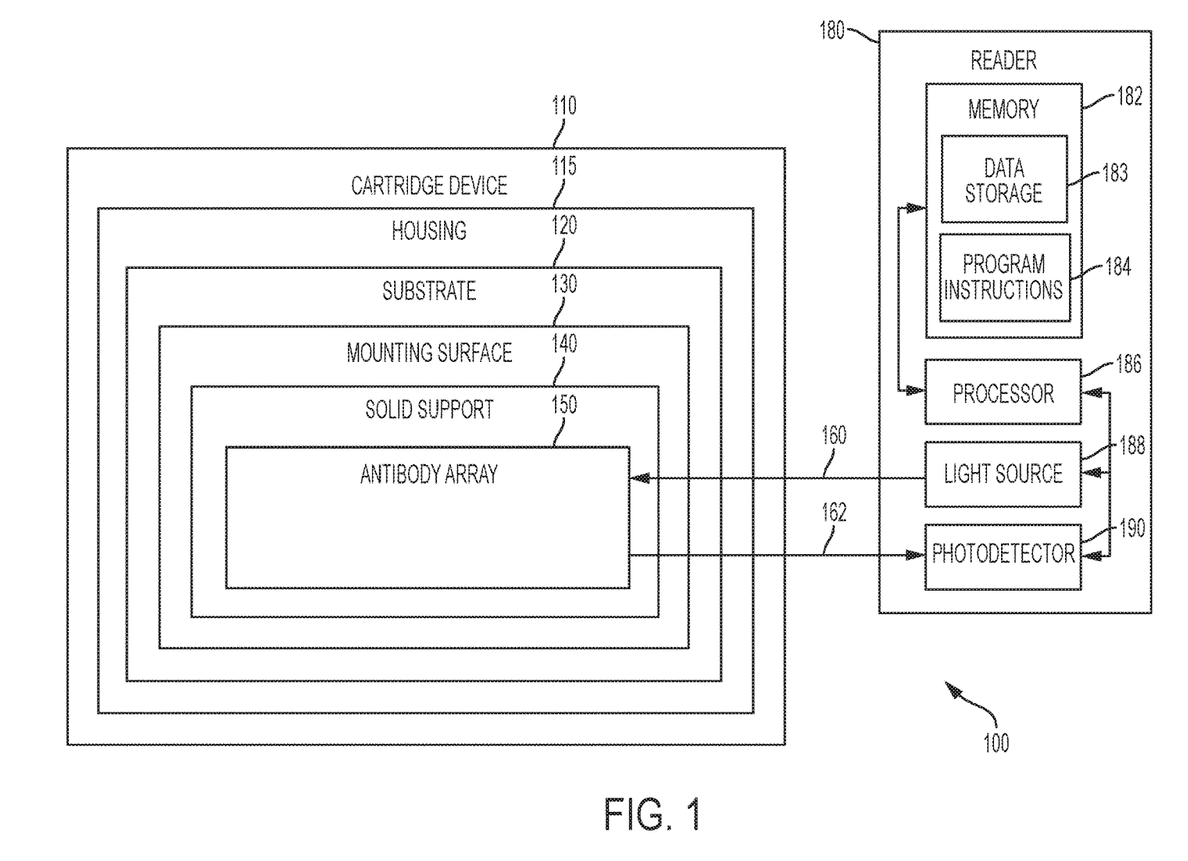
FIG. 1 is a block diagram of an example system that includes a cartridge device in wireless communication with a reader device, in accordance with an example embodiment.

FIG. 1 is a block diagram of a system 100 that includes a cartridge device 110 and a reader 180. The cartridge device 110 includes a substrate 120 that is configured to be mounted to a solid support 140 that includes an antibody array 150. Substrate 120 is housed in a protective housing 115. Substrate 120 could be formed from a polymeric material, for example, that is transparent to interrogating incident light of the reader. The housing could also be formed from a polymeric material that is transparent to the interrogating incident light of the reader or may include a opening or window of such polymeric material, allowing the interrogating incident light of the reader to reach substrate 120. The substrate 120 has a mounting surface 130 for mounting the solid support 140 which includes an antibody array 140. Disposed on or within the solid support 140 is an addressable array 150 of at least one type of antibody that is specific to a target antigen. Protein M, a competitor to the target antigen for binding to the antibody, can be pre-complexed to the antibody array prior to addition of the liquid sample or introduced after complex formation between the target antigen and the antibody. Protein M and each type of antibodies specific to a target antigen have a detectable label (e.g., fluorophore) that is different from each other. The optical properties of the antibody array undergo a detectable change (e.g., a change in the level of fluorescence of each of the detectable labels) when the antibodies interact with the target antigen and Protein M. The detectable change can be related to the antibody. Protein M, or both as well as the presence, absence, or concentration of the target antigen.

Reader 180 can also include a computing system with a processor 186 in communication with a memory 182. Memory 182 is a non-transitory computer-readable medium that can include, without limitation, magnetic disks, optical disks, organic memory, and/or any other volatile (e.g. RAM) or non-volatile (e.g. ROM) storage system readable by the processor 186. The memory 182 can include a data storage 183 to store indications of data, such as output readings (e.g., from the antibody array), program settings (e.g., to adjust behavior of the substrate 110 and/or reader 180), etc. The memory 182 can also include program instructions 184 for execution by the processor 186 to cause the reader 180 to perform processes specified by the instructions 184. For example, the program instructions 184 can cause reader 180 to perform any of the operations described herein.

As shown, the reader device 180 can include a light source 188 configured to transmit incident light 160 to the cartridge device 110 and a photodetector 190 configured to receive light 162 from the cartridge device 110. The incident light 160 can be used to optically interrogate the antibody array 150 so as to detect interaction of the antibody array 150 with the target antigen in the liquid sample and Protein M. For example, the incident light can include a wavelength that excites a fluorophore in the antibody array 150 such that the antibody array 150 and any Protein M complexed to the antibody array emit fluorescence light. The fluorescence light can be included in the received light 162 and detected by the photodetector 190. Based on the light emitted from the antibody array 150 and Protein M that is detected by the photodetector 190, the reader 180 can detect the target antigen. Moreover, the detection could be quantitative. For example, an intensity, wavelength, or other characteristic of the received light 162 can be used for ratiometric determinations which in turn can be used to determine the concentration of the target antigen in the liquid sample. Alternatively, the concentration of the target antigen can be inferred by monitoring the kinetics of the signal change as Protein M is competed off of the antibody. The components of the skin-mountable device 110 may be transparent to the incident light 160 and the light 162 emitted by the nanosensors in response to the incident light 160.

In one embodiment, a system is provided. The system includes a device including a cartridge which includes a substrate for the detection of antigens as described above and a reader. In some embodiments, the cartridge is a disposable unit that plugs into the reader. Once the readings have been determined, the cartridge can be removed from the reader and disposed of. In some embodiments, the cartridge is preloaded with reagents, e.g., washing and/or buffer solutions or dried chemicals for preparing such solutions, and antibody probes specific to a disease such that the operator can insert different cartridges into the reader device for different diseases. In some embodiments, the cartridge further includes microfluidic pumps or structures. For operation, a liquid sample such as saliva, blood, sputum, or urine is applied or placed, e.g., injected, into the cartridge. The binding assay for the detection of antigens is performed within the cartridge. The cartridge containing the sample is then inserted into the device, whereby the detection and/or quantitation of a target antigen occurs.

The system may further include one or more data collection systems for interrogating, in a non-invasive manner, the array. In one example, the system includes a detector configured to detect a response signal transmitted from the array. The response signal can include both an binding response signal, which can be related to the interaction of the one or more target antigens and/or Protein M with the antibodies, and a background noise signal. For example, the antibodies and/or Protein M may include a fluorescent labels configured to produce a fluorescence signal in response to a binding interaction or chemical reaction initiated, at least in part, to the presence of the target antigen.

In some examples, the system may include an interrogating signal source for transmitting an interrogating signal in the form of an excitation light that can penetrate into the array following exposure to the antigen and/or protein M and a detector for detecting a response signal that is transmitted from the array, in response to the interrogating signal. The interrogating signal can be any kind of optical signal that results in a response signal that can be used to detect the binding or interaction of the antigen and/or Protein M with the antibodies. In one example, in which the array includes fluorescence labels, the interrogating signal is an optical signal with a wavelength that can excite the fluorophore in the sensor (e.g., a wavelength in the range of about 400 to about 1000 nanometers), and the response signal is fluorescence radiation from the fluorophore that can reach the detector.

In some cases, an interrogating signal is not necessary to measure binding events and, therefore, the system may not include a light source 188. For example, arrays can include autofluorescent or luminescent labels that will automatically emit a response signal indicative of the binding or displacement of the antigen and/or Protein M to the array, without the need for an interrogating signal or other external stimulus. In some examples, the antibody array may include a chemiluminescent marker configured to produce a response signal in the form of luminescence radiation produced in response to a chemical reaction initiated, at least in part, to the binding of the target antigen or Protein M to the array.

Additionally, the system may further include a modulation source configured to modulate the antigen and/or Protein M response signal. The modulation source can be configured to modulate the antigen response signal differently than the background noise signal. To this end, the modulation may help to discern between the target antigen and Protein M and, essentially, everything else in the body by, for example, increasing the signal-to-noise ratio. Generally, the modulation may include any spatial, temporal, spectral, thermal, magnetic, mechanical, electrical, acoustic, chemical, or electrochemical, etc. modulation technique or any combination thereof.

In some scenarios, it may also be useful to detect and distinguish both the antigen and/or Protein M response signal—related to antibody array bound to or interacting with target antigen and/or Protein M—and an "unbound" antibody array signal-related to antibodies bound to or interacting with target antigen(s). For example, in some measurement or characterization schemes, it may be useful to determine the percentage of array elements present that are bound to the target antigens and/or Protein M. In such cases, the modulation source may be configured to modulate the antigen and/or Protein M response signal differently than the unbound array signal.

The elements of the system, namely the type of modulation, the types of antibodies, the types of detection labels, and target antigens may all be interrelated. Ultimately, the type of arrays used to detect a particular target antigen may depend, to some extent, on the characteristics of the target antigen (i.e., type, size, shape, affinities, etc.) and the chosen type of modulation (i.e., spatial, spectral, thermal, magnetic, mechanical, chemical, etc.).

III. Illustrative Cartridge Device

The cartridge device can include the following components: (1) a solid support having an addressable array of at least one type of antibody immobilized thereon, wherein each type of antibody is specific for a target antigen and forms a binding complex in the presence of the target antigen, and wherein each type of antibody has a detectable label that is different; (2) a substrate having a mountable surface for the solid support; (3) a protective housing for the substrate; and (4) Protein M for competitively displacement of the target antigen in the complex. Both Protein M and each type of antibody have a detectable label which is different from each other. In some embodiments, Protein M is included as a reagent in the cartridge device where it is added after introduction of the liquid sample into the cartridge device. In other embodiments, Protein M is introduced into the cartridge device after the introduction of the liquid sample into the cartridge device. In some embodiments, Protein M is pre-complexed to the antibody array prior to introduction of the liquid sample into the cartridge device.

In another embodiment, a device is provided for the rapid, multiplexed, customizable detection of antigens for which an antibody exists or can be developed, and need not be limited by the antibody isotype or the species from which the antibody originated. In one embodiment, the device includes a handheld reusable reader and a disposable plug-in cartridge which includes a chip for the detection of antigens. The reader can include a graphical user interface operated by touchscreen. In one embodiment, the cartridge includes a solid support having immobilized antibody probes (sensor chip) which mounted on a substrate (or chip carrier) and protected with a housing such as a plastic (e.g., polypropylene) housing. In some embodiments, the chip may include an array of antibody sites and reference sites.

a. Protein M

Protein M, also referred to as MG281 protein, is a class of antigen derived from mycoplasma, a genus of bacteria that includes species that are pathogenic to humans. Protein M or fragments thereof were found to bind non-specifically to immunoglobulins with high affinity and compete non-specifically for access to the antibody combining site. Protein M and fragments were used for purifying or isolating immunoglobins as well as in vaccines as treatment against mycoplasma infections, myeloma as well as autoimmune disease. The sequence, preparation, purification and isolation of Protein M and fragments thereof recombinantly or from mycobacteria are described in WO 2014/014897 and Grover et al., Science, 2014, Vol. 343, pp. 656-661, which is incorporated by reference in its entirety. Recombinant Protein M having various pre-determined binding specificity and affinity can be generated by any suitable method. In a representative example for generating Protein M, E. coli BL21 can be transfected with a suitable plasmid encoding Protein M or a fragment thereof wherein the expression can be induced by the addition of a suitable agent, e.g., isopropyl B-D-1-thiogalactopyranoside. The transfected cells are then harvested, lysed, and the resultant recombinant protein is then purified by affinity chromatography.

In one embodiment, a recombinant Protein M or fragment thereof is employed for complexing with the array. In other embodiments, dimeric Protein M may be used. Dimeric Protein M can be prepared by expressing a vector including a sequence encoding a dimeric form of Protein M and purifying the recombinant protein for instance.

b. Antibody and Antibody Array

In one embodiment, antibodies that specifically bind to target antigens to form an antibody/antigen complex are used to make the array. As defined herein, "antibody," can mean a polyclonal or monoclonal antibody. Further, the term "antibody" means intact immunoglobulin molecules, chimeric immunoglobulin molecules, or Fab or F(ab')$_2$ fragments. Such antibodies and antibody fragments can be produced by techniques well known in the art which include those described in Harlow and Lane (Antibodies: A Laboratory Manual Cold Spring Harbor Laboratory, Cold Spring Harbor, N.Y. (1989)) and Kohler et al. (Nature 256: 495-97 (1975)) and U.S. Pat. Nos. 5,545,806, 5,569,825 and 5,625,126, incorporated herein by reference. Correspondingly, antibodies, as defined herein, also include single chain antibodies (ScFv), comprising linked $V_H$ and $V_L$ domains and which retain the conformation and specific binding activity of the native idiotype of the antibody. Such single chain antibodies are well known in the art and can be produced by standard methods. (see, e.g., Alvarez et al., Hum. Gene Ther. 8: 229-242 (1997)). The antibodies of the present invention can be of any isotype IgG, IgA, IgD, IgE and IgM. Antigen," as used herein, includes substances that upon administration to a vertebrate, e.g., human, are capable of eliciting an immune response, thereby stimulating the production and release of antibodies that bind specifically to the antigen.

Antigen, as defined herein, includes molecules and/or moieties that are bound specifically by an antibody to form an antigen/antibody complex. Representative antigens may be, but are not limited to being, peptides, polypeptides, proteins, nucleic acids. DNA, RNA, saccharides, combinations thereof, fractions thereof, or mimetics thereof.

The term "bind," as used herein, means the well understood antigen/antibody binding as well as other nonrandom association between an antigen and an antibody. "Specifically bind," as used herein describes an antibody or other ligand that does not cross react substantially with any antigen other than the antigen, or antigens, specified. For instance, "specific binding" of an antibody to a class of antigens having an epitope in common is contemplated.

In one embodiment, the antibodies are arranged as an array or microarray on a solid support. "Microarray" or "array" as used herein, is an ordered arrangement of array elements (e.g., antibodies that are specific for a target antigen) capable of binding other species, e.g., target antigen and Protein M. The elements can be arranged so that there are at least one or more different array elements, at least 10 array elements, at least 100 array elements, or 10,000 array elements, on a 1 $cm^2$ substrate surface. In some embodiments, array generated on the solid support, e.g., membrane, can have a density of at least 5 spots/$cm^2$, at least 10, 20, 30, 40, 50, 60, 70, 80, 90, 100, 110, 120, 130, 140, 150, 160, 170, 180, 190, 200, 210, 220, 230, 250, 275, 300, 325, 350, 375, 400, 425, 450, 475, 500, 550, 600, 650, 700, 750, 800, 850, 900, 950, 1000, 2000, 3000, 4000, 5000, 6000, 7000, 8000 or 9000 spots/$cm^2$ or at least 10,000 spots/$cm^2$. Methods for generating microarrays have been described. See, for instance, U.S. Patent publication no. 2003/0153013, which is incorporated by reference in its entirety.

c. Solid Support and Substrate

A solid support generally refers to solid material to which the antibodies are physically attached, thereby immobilizing the antibodies. The solid support can be provided in any suitable form or configuration such as a slide, plate, chip, well, microwell plate, or membrane. A solid support can be, but is not limited to, a membrane, sheet, gel, glass, plastic or metal. Immobilized components may be associated with a solid support by covalent bonds and/or via non-covalent attractive forces such as hydrogen bond interactions and steric capture, hydrophobic attractive forces and ionic forces, for example. In some embodiments, the solid support can be made from an organic material such as a polymer. Suitable, but not limiting examples of polymer include hydrophilic polyethylenes, polystyrenes, polypropylenes, acrylates, methacrylates, polycarbonates, polysulfones, polyester-ketones, poly- or cyclic olefins, polychlorotrifluoroethylene, polyethylene terephthalate, or polymer compositions such as described in U.S. Pat. Nos. 6,653,425, 6,166,125, 6,593,415, or U.S. Pat. No. 6,590,036, incorporated herein by reference. In the case of gel based immobilization, one can use steric capture where one could immobilize by casting the antibodies into a hydrogel with typical pore sizes smaller than the hydrodynamic radius of the antibody, limiting its ability to escape from the gel layer.

In other embodiments, the solid support is made from inorganic materials including a variety of glass types, such as a silicate, aluminosilicate, borosilicate, or boro-aluminosilicate; glass-ceramic, ceramic, semiconductor or crystalline materials such as silicon also may be employed. The particular glass type may be selected to impart desired material characteristics, such as coefficients of thermal expansion (CTE), durability, or chemical reactivity (e.g., leaching or background signal/noise), which are adapted to or satisfy specific parameters for manufacture or certain assay protocols or conditions.

In other embodiments, glass, glass-ceramics, or high-purity fused silica, which have properties for light transmission or optical waveguiding, or organic materials, such as optically clear polymers or plastics of uniform index having functional groups that do not generate a high background auto-fluorescence at interrogation wavelengths or scatter centers from crystallite phase separations can be used for the solid support.

The substrate of the cartridge device can be constructed from a variety of materials, including metals, ceramics, semiconductors, organics, polymers, and composites. The substrate includes a surface to which the solid support is attached or integrally formed. In some embodiments, the substrate includes a suitable adhesive material to secure the solid support. In some embodiments, both the substrate and adhesive can constructed with materials that are optically invisible so as to not interfere with transmission of the incident light from the reader or optical detection of fluorescent signals from the array.

d. Detectable Labels

In one embodiment, Protein M and each type of antibody that is specific to a target antigen has a detection label, e.g., a fluorophore, that is different from each other. When the labeled antibodies interact with the target antigen and labeled Protein M, a detectable change, e.g., in optical absorption, reflectivity or fluorescence, can be measured. A "detection label" generally refers to a chemical compound, molecule, ion, or particle that directly possesses or indirectly comes to possess a detectable signal. Particles may include microparticles and nanoparticles which may be further labeled. Compounds or molecules may include fluorophores or auto-fluorescent or luminescent markers. In some embodiments, the detection label can emit an optical signal. Numerous labels are known by those of skill in the art and include, but are not limited to, particles, fluorophores, haptens, enzymes and their colorimetric, fluorogenic and chemiluminescent substrates and other labels that are described in Richard P. Haugland, Molecular Probes Handbook of Fluorescent Probes and Research Products (9th edition, CD-ROM, (September 2002), which is herein incorporated by reference.

In some embodiments, the detection label is a fluorophore. As defined herein, a "fluorophore" is a molecule (e.g., colored dye) which emits light at a specific range of wavelengths or segment of the spectrum after excitation by light of a lower wavelength or lower range of wavelengths versus the emission wavelengths. Different types of fluorophores emit energy at different wavelengths or spectral ranges. A fluorophore label can be any chemical moiety that exhibits an absorption maximum at or beyond 280 nm, and when covalently attached to the aptamer or other reagent retains its spectral properties. The choice of the fluorophore will determine the absorption and fluorescence emission properties of the antibody conjugate and Protein M conjugate. Physical properties of a fluorophore label include spectral characteristics (absorption, emission and stokes shift), fluorescence intensity, lifetime, polarization and photo-bleaching rate all of which can be used to distinguish one fluorophore from another.

Representative examples of fluorophores include, without limitation: xanthene (rhodol, rhodamine, fluorescein and derivatives thereof) coumarin, cyanine, pyrene, oxazine and borapolyazaindacene. Sulfonated xanthenes, fluorinated xanthenes, sulfonated coumarins, fluorinated coumarins and sulfonated cyanines are useful. Specific examples of fluorophore detection labels include, without limitation, fluorescein, coumarins, rhodamines, 5-TMRIA (tetramethylrhodamine-5-iodoacetamide), (9-(2(or 4)-(N-(2-maleimdylethyl)-sulfonamidyl)-4(or 2)-sulfophenyl)-2,3,6, 7,12,13,16,17-octahydro-(1-H,5H,11H,15H-xantheno(2,-3, 4-ij:5,6,7-i'j')diquinolizin-18-ium salt) (TEXAS RED), 2-(5-(1-(6-(N-(2-maleimdylethyl)-amino)-6-oxohexyl)-1,3-dihydro-3,3-dimet-hyl-5-sulfo-2H-indol-2-ylidene)-1,3-propyldienyl)-1-ethyl-3,3-dimethyl-5-s-ulfo-3H-indolium salt (Cy3). N,N'-dimethyl-N-(iodoacetyl)-N'-(7-nitrobenz-2-oxa-1,3-diazol-4-yl)ethyle-nediamine (IANBD amide), N-((2-(iodoacetoxy)ethyl)-N-methyl)amino-7-nitrobenz-2-oxa-1,3-diazole (IANBD ester), 6-acryloyl-2-dimethylaminonaphthalene (acrylodan), pyrene, 6-amino-2,3-dihydro-2-(2-((iodoacetyl)amino)ethyl)-1,3-dioxo-1H-benz(de)isoquinoline-5,8-disulfonic acid salt (lucifer yellow), 2-(5-(1-(6-(N-(2-maleimdylethyl)-amino)-6-oxohexyl)-1,3-dihydro-3,3-dimet-hyl-5-sulfo-2H-indol-2-ylidene)-1,3-pentadienyl)-1-ethyl-3,3-dimethyl-5-su-lfo-3H-indolium salt (Cy™5), 4-(5-(4-dimethylaminophenyl)oxazol-2-yl)phenyl-N-(2-bromoacetamidoethyl) sulfonamide (Dapoxyl® (2-bromoacetamidoethyl)sulfonamide)), (N-(4,4-difluoro-1,3,5,7-tetramethyl-4-bora-3a,4a-diaza-s-indacene-2-yl)i-odoacetamide (BODIPY 507/545 IA), N-(4,4-difluoro-5,7-diphenyl-4-bora-3a,4a-diaza-s-indacene-3-propionyl)-N-iodoacetylethylenediamine (BODIPY 530/550 IA), 5-((((2-iodoacetyl)amino)ethyl) amino)napthalene-1-sulfonic acid (1,5-IAEDANS), and carboxy-X-rhodamine, 5/6-iodoacetamide (XRIA 5,6). Another example of a label is BODIPY-FL-hydrazide.

In some embodiments, the detection labels include lanthanides such as europium (Eu3+) and terbium (Tb3+), as well as metal-ligand complexes of ruthenium [Ru(II)], rhenium [Re(I)], or osmium [Os(II)], typically in complexes with diimine ligands such as phenanthroline.

The detection labels used in the current methods and compositions can be attached through any suitable means including chemical means, such as reduction, oxidation, conjugation, and condensation reactions. For example, any suitable reactive group on the antibody and Protein M can be used to attach the detection labels, e.g., a fluorophore, to a naturally occurring or engineered thiol group present in the aptamer. For instance, succinimide ester derivatives of fluorophores can be used to label the antibody and/or Protein M. See Richieri, G. V. et al., J. Biol. Chem., 267: 23495-501 (1992) which is hereby incorporated by reference.

e. Representative Antigen Detection Method

In one embodiment, a method is provided for detecting a target antigen. The method includes contacting a labeled antibody for a target antigen with a sample believed to include the target antigen under conditions that allow the target antigen and the labeled antibody complex to bind and form a first complex, wherein the labeled antibody is immobilized on a solid support; washing the solid support, contacting the solid support with labeled Protein M under conditions that allow the labeled Protein M to bind to any remaining labeled antibody that is not complexed, if any, to form a second complex; and detecting for the presence and/or amount of the second complex.

Figure 2:
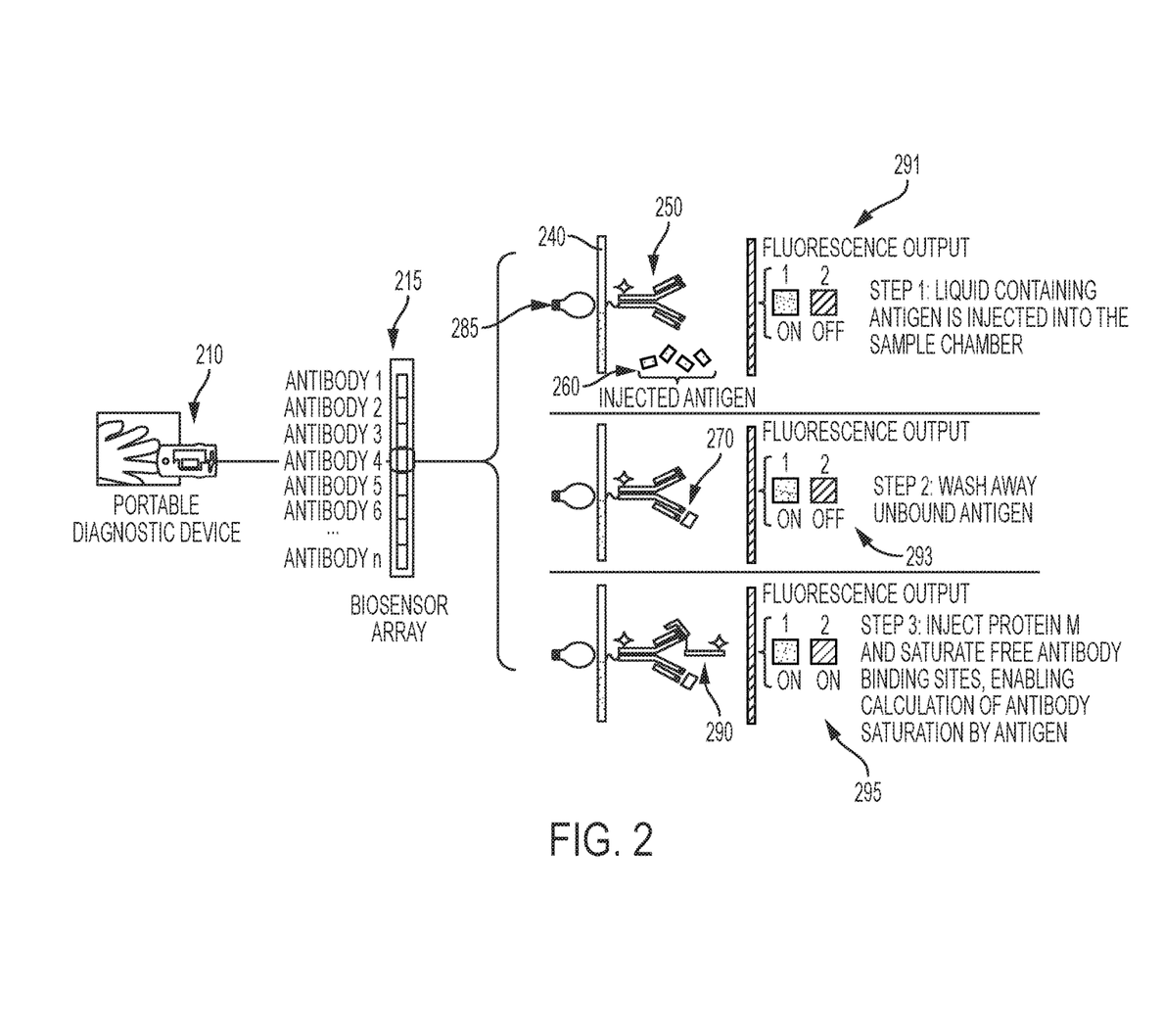
FIG. 2 is an illustration of an example method of detecting a target antigen.

As shown in FIG. 2, the optical output 291 of the antibody 250 is measured after incident excitation light is directed to the solid support but before the addition of sample. A liquid sample (blood) drawn by the cartridge 210 is contacted with the labeled antibody 250 immobilized on a solid support 240. The sample includes target antigen 260 which forms a first complex 270 on the solid support. A wash step (not shown) can be included to wash away unbound antigen. The optical output 293 of the complex of antibody and target antigen is measured after incident excitation light is directed to the solid support. A solution including labeled Protein M 290 is then applied to the solid support, whereby the Protein M 290 binds to any remaining labeled antibody site that is not complexed with antigen. A wash step (not shown) can be included to wash away unbound Protein M. The optical output 295 after addition of Protein M 290 can be measured after incident excitation light is directed to the solid support. In quantitation mode wherein the antigen is allowed to bind the antibody but not fully saturate all antibody binding sites, the ratiometric measurement of the output signals 291, 293 and 295 allows for the ratiometric calculation of antibody saturation by the antigen and determination of the concentration of the target antigen in the sample. In detection mode, the absence or presence of signal 290 with the presence of signal 250 can be used to determine whether antigen can or cannot be detected in the sample. Generally, if the antigen concentration is high enough, it will saturate the antibody (zero signal from Protein M) and one can then only conclude that the antigen is above a certain concentration. Likewise, if the antigen is allowed to incubate for a long time and one sees 100% signal from Protein M, then one can only conclude that the antigen is undetectable.

In another embodiment, a method is provided for detecting a target antigen. The method includes contacting a labeled antibody for a target antigen with labeled dimeric Protein M under conditions that allow a labeled dimeric Protein M and labeled antibody to form a first complex, wherein the labeled antibody is immobilized on a solid support; washing the solid support; contacting the solid support with a sample believed to include the target antigen under conditions that allow a target antigen and labeled antibody to bind and form a second complex when target antigen is present at a sufficient concentration to displace the labeled dimeric Protein M from the first complex; washing the solid support; and detecting for the presence and/or amount of the first complex. If the target antigen is present at a sufficiently high concentration, it competitively displaces Protein M from the first complex to form the second complex within seconds or minutes, resulting in the loss of Protein M fluorescence signal at a specific spot on the array. In this embodiment, the number of antigens that are simultaneously detected is limited by the size of the array and the volume of sample that is delivered to the array.

Figure 3:
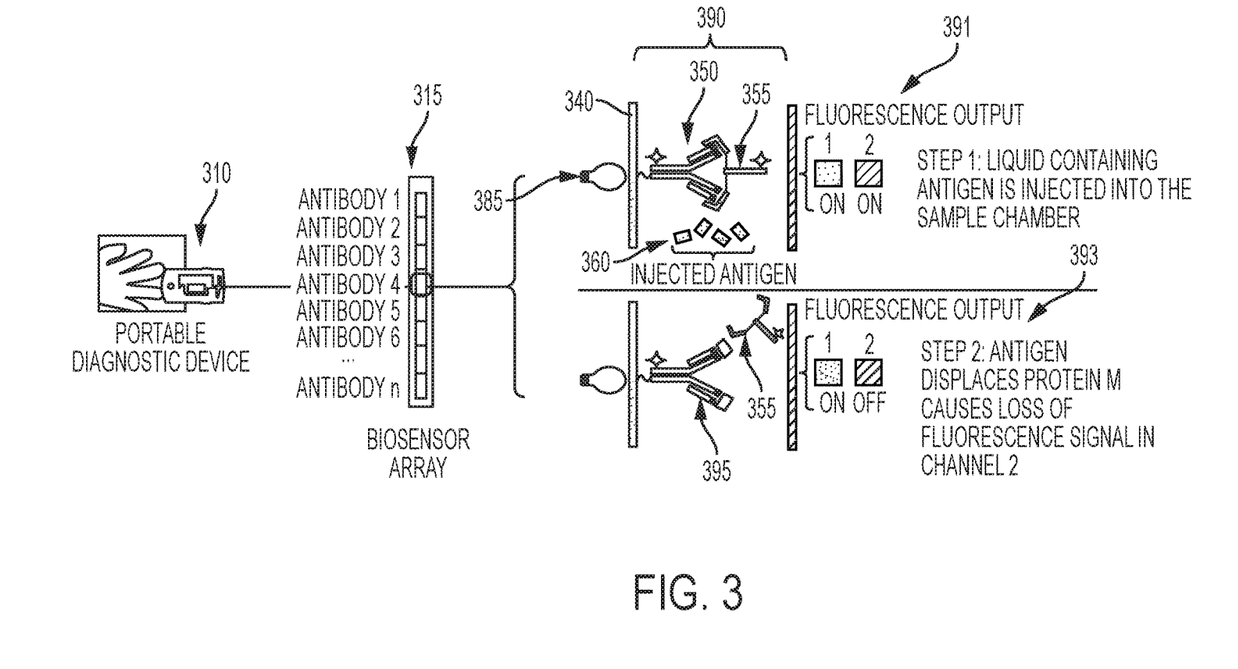
FIG. 3 is an illustration of an example method of detecting a target antigen.

As shown in FIG. 3, a labeled antibody 350 immobilized on a solid support 340 is contacted with labeled dimeric Protein M 355 to form a first complex 390 on the solid support. A wash step (not shown) can be included to wash away unbound dimeric protein. The optical output 391 of the first complex is measured after incident excitation light 385 is directed to the solid support. A sample is then applied to the solid support 340, and the rate at which dimeric Protein M 355 dissociates from the antibody in the presence of sample or after a defined period of incubation with the sample is used to calculate the concentration of antigen or determine its presence in the sample based on the ratiometric measurement of the output signals 391 and 393. The dynamic range of each antibody can be dependent on its intrinsic affinity for a particular antigen. Thus a high concentration of antigen can mean a concentration high enough to force detectable dissociation of dimeric Protein M. A wash step (not shown) can be included to wash away unbound antigen and dissociated dimeric Protein M 355. The optical output 393 of the second complex is measured after incident excitation light 385 is directed to the solid support. A displacement of the labeled dimeric Protein M by the target antigen would result in the loss of output signal from the dimeric Protein M. The ratiometric measurement of the output signals 391 and 393 allows for the calculation of antibody saturation by the antigen and determination of the concentration of the target antigen in the sample.

In some embodiments, the antibodies are arrayed on the solid support at addressable sites and the user applies a liquid sample such as saliva, urine, blood or water. In some embodiments, fluorescence or bioluminescence serve as the basis for detection. In some embodiments, Protein M and dimeric Protein M is labeled with a fluorophore of differing excitation/emission properties relative to the antibody, enabling ratiometric measurement. In some embodiments, the detection labels are lanthanides. In some embodiments, a surface sensitive technique is employed (e.g., total internal reflectance excitation) which allows observation of the binding kinetics in real time as the fluorescent solutions do not contribute substantially to background. In some embodiments, mixtures of different antibodies, each labeled with different label, e.g., lanthanide-based fluorophores, nanocrystals, rare-earth dopants in ceramics, defects in wide bandgap semiconductors, and organic dyes with disparate spectral fingerprint) can be complexed with fluorescently-labeled Protein M, enabling multiplexed detection of more than one target antigen. In this embodiment, the extent of the detection of antigens is limited to the number of antigens that can be simultaneously detected is defined by the number of unique barcodes available on the array.

IV. Example Substrate/Reader Interactions

Figure 4A:
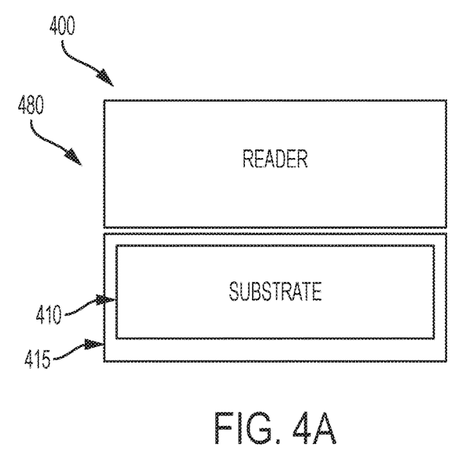
FIG. 4A is an example system that includes a cartridge device and a proximately located reader device, in accordance with an example embodiment.

FIG. 4A is a diagram of an example system 400. A reader 480 is positioned proximate to a substrate 410 which is housed in housing 415. It is noted that relative dimensions in FIG. 4A are not necessarily to scale, but have been rendered for purposes of explanation.

Figure 4B:
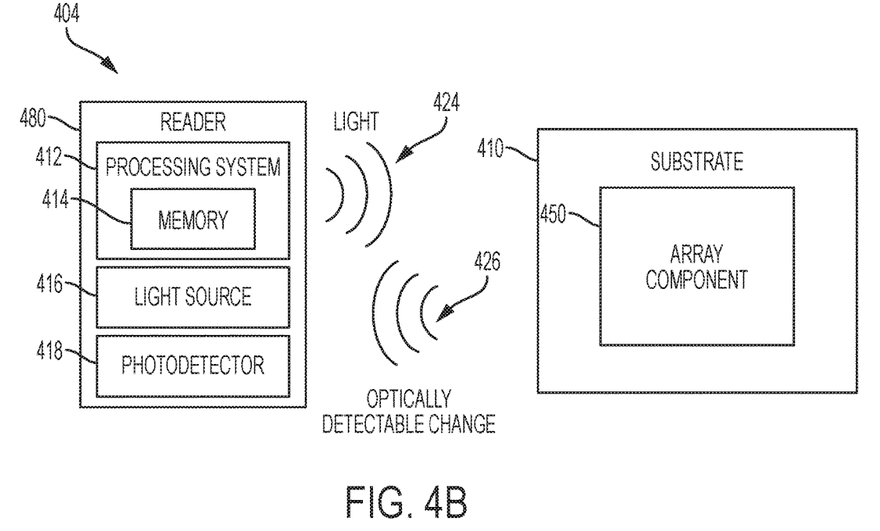
FIG. 4B is a block diagram of an optical system operated by a reader device capable of detecting an optically-detectable change in a substrate, in accordance with an example embodiment.

In one embodiment, the substrate 410 can include antibody array 450. FIG. 4B is a block diagram of a system described in connection with substrate 410 and reader 480 in FIG. 4A. System 404 includes a substrate 410 that is interrogated by a reader 480 to obtain one or more measurements related to an antigen in the liquid sample. An array component 450 configured to undergo an optically-detectable change 426 related to the antigen, Protein M, or both can be included with substrate 410. The optically-detectable change 426 may include a change in at least one of optical absorption, reflectivity, or fluorescence.

The array component 450 can be interrogated by a light source 416 in the reader 480. More particularly, the reader 480 may include a light source 416 configured to direct light 424 toward the array component 450 of the substrate 410, and a photodetector 418 configured to detect light 426 from the array component 450. For example, the substrate 410 may include fluorophore labeled antibodies and fluorophore labeled Protein M as an array component 450 that undergoes differential fluorescence upon interaction with an antigen. The reader 480 can be placed proximate to the substrate 410 so that the light source 416 may provide light 424 to the array component 440. If the antigen is present, the array component 440 may undergo a differential fluorescence, and the fluorescence 426 may be detected by the photo detector 418. For instance, if target antigen is present, a portion of Protein M complexed with the antibodies can be displaced and the fluorescence emission difference for Protein M before and after displacement can be measured. Alternatively, if target antigen is present, a first complex between the targen antigen and antibodies can be formed. Upon addition of Protein M, any remaining uncomplexed antibodies can form a second complex with Protein M. The fluorescence emission differences of Protein M before (no emission) and after addition of Protein M can be measured.

V. Example Readers

The system includes a reader device ("reader"), that is configured to detect the interaction between the substrate and the antigen in the sample. The reader can be a smart phone, digital assistant, or other portable computing device with wireless connectivity sufficient to communicate with the substrate. In some examples, the reader is positioned proximate to the substrate only when a measurement is desired. In other examples, the reader is removably mounted proximate to the substrate so that the antigen-substrate interaction can be detected on demand or continuously without having to position the reader.

After receiving antigen-related data from the substrate, the reader can utilize the data; e.g., process, present, store, communicate, etc. For example, the reader can process the antigen-related data to generate an antigen concentration, and the display device can present the antigen concentration to the user.

In some embodiments, the reader may evaluate the antigen-related data and display a visual indication of the measured parameters. For example, the reader may compare an antigen concentration to a low- and/or high-antigen threshold(s) to determine, respectively, whether the antigen concentration is too high or low.

VI. Example Operations

In some embodiments, the present disclosure provides a method for operating a system including a substrate and a reader to measure an antigen concentration of a fluid in the skin.

Figure 5:
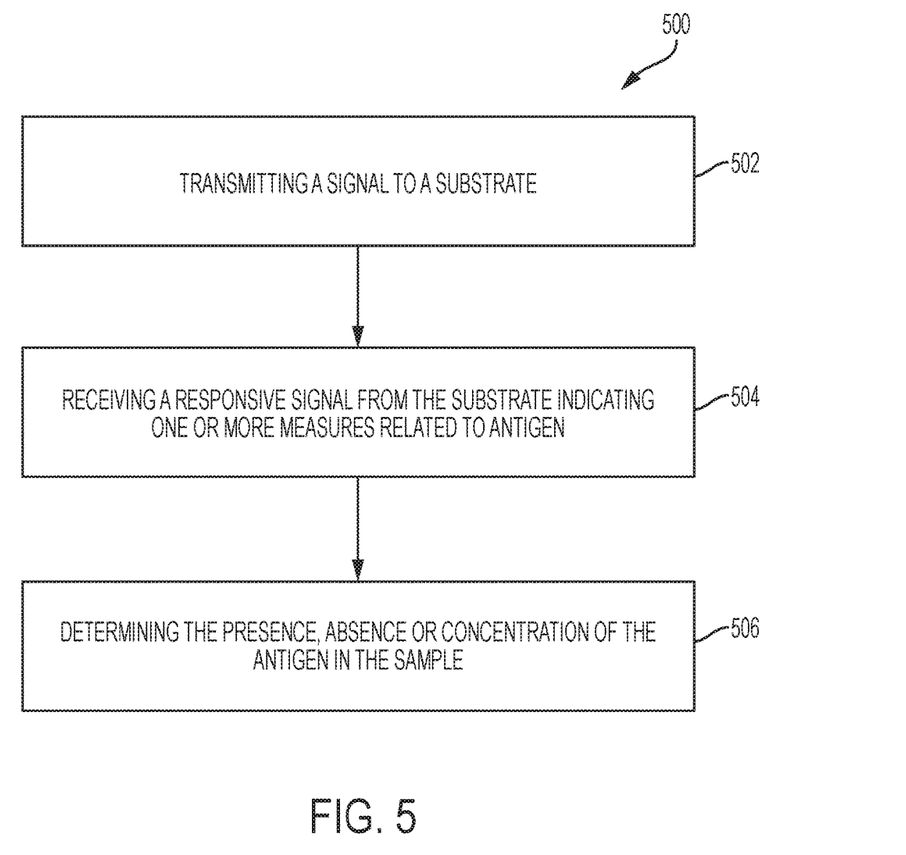
FIG. 5 is a flowchart of an example method for operating a system with an external reader and a substrate to measure an antigen in a sample.

FIG. 5 is a flowchart of a method 500 for operating a system including a reader and a cartridge. The method includes transmitting a signal to a substrate (502). In some examples, the signal may be optical, such as visible light or fluorescent light. The method further includes receiving a responsive signal from the substrate (504). The responsive signal may indicate one or more measurements related to an antigen in a sample. For example, when the substrate includes an antenna, the responsive signal may an optical signal, such as a change in optical absorption, reflectivity, or fluorescence. In some embodiments, the method may further include determining the presence, absence or concentration of an antigen in the sample (506). In embodiments where the substrate includes a component configured to undergo an optically-detectable change related to an antigen, the presence, absence or concentration of the antigen, may be determined.

VII. Conclusion

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The above detailed description describes various features and functions of the disclosed systems, devices, and methods with reference to the accompanying figures. In the figures, similar symbols typically identify similar components, unless context dictates otherwise. The example embodiments described herein and in the figures are not meant to be limiting. Other embodiments can be utilized, and other changes can be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the ladder diagrams, scenarios, and flow charts in the figures and as discussed herein, each block and/or communication may represent a processing of information and/or a transmission of information in accordance with example embodiments. Alternative embodiments are included within the scope of these example embodiments. In these alternative embodiments, for example, functions described as blocks, transmissions, communications, requests, responses, and/or messages may be executed out of order from that shown or discussed, including substantially concurrent or in reverse order, depending on the functionality involved. Further, more or fewer blocks and/or functions may be used with any of the ladder diagrams, scenarios, and flow charts discussed herein, and these ladder diagrams, scenarios, and flow charts may be combined with one another, in part or in whole.

A block that represents a processing of information may correspond to circuitry that can be configured to perform the specific logical functions of a herein-described method or technique. Alternatively or additionally, a block that represents a processing of information may correspond to a module, a segment, or a portion of program code (including related data). The program code may include one or more instructions executable by a processor for implementing specific logical functions or actions in the method or technique. The program code and/or related data may be stored on any type of computer readable medium such as a storage device including a disk or hard drive or other storage medium.

The computer readable medium may also include non-transitory computer readable media such as computer-readable media that stores data for short periods of time like register memory, processor cache, and random access memory (RAM). The computer readable media may also include non-transitory computer readable media that stores program code and/or data for longer periods of time, such as secondary or persistent long term storage, like read only memory (ROM), optical or magnetic disks, compact-disc read only memory (CD-ROM), for example. The computer readable media may also be any other volatile or non-volatile storage systems. A computer readable medium may be considered a computer readable storage medium, for example, or a tangible storage device.

Moreover, a block that represents one or more information transmissions may correspond to information transmissions between software and/or hardware modules in the same physical device. However, other information transmissions may be between software modules and/or hardware modules in different physical devices.

The particular arrangements shown in the figures should not be viewed as limiting. It should be understood that other embodiments can include more or less of each element shown in a given figure. Further, some of the illustrated elements can be combined or omitted. Yet further, an example embodiment can include elements that are not illustrated in the figures.

It will be readily understood that the aspects of the present disclosure, as generally described herein, and illustrated in the figures, can be arranged, substituted, combined, separated, and designed in a wide variety of different configurations, all of which are explicitly contemplated herein. While various aspects and embodiments have been disclosed herein, other aspects and embodiments will be apparent to those skilled in the art.

Example methods and systems are described above. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features. Reference is made herein to the accompanying figures, which form a part thereof. In the figures, similar symbols typically identify similar components, unless context dictates otherwise. Other embodiments may be utilized, and other changes may be made, without departing from the spirit or scope of the subject matter presented herein. The various aspects and embodiments disclosed herein are for purposes of illustration and are not intended to be limiting, with the true scope and spirit being indicated by the following claims.

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The invention claimed is:

1. A device comprising:
   a solid support having an addressable array of at least one type of antibody, each type of antibody having a detectable label that is different, wherein each type of antibody is immobilized onto the solid support, wherein each type of antibody is specific for a target antigen and forms a complex in the presence of said target antigen;
   labeled dimeric Protein M bound to said each type of antibody, wherein said dimeric Protein M has a detectable label that is different from said detectable label of said each type of antibody, and wherein said dimeric Protein M can be competitively displaced by the target antigen;
   a substrate having a mountable surface for the solid support; and
   a protective housing for the substrate.

2. A system comprising:
   (a) a cartridge device comprising:
      a solid support having an addressable array of at least one type of antibody immobilized thereon, wherein each type of antibody is specific for a target antigen and forms a complex in the presence of the target antigen, and wherein each type of antibody has a detectable label that is different;
      labeled dimeric Protein M bound to said each type of antibody, wherein said dimeric Protein M has a detectable label that is different from said detectable label of said each type of antibody, and wherein said dimeric Protein M can be competitively displaced by the target antigen;
      a substrate having a mountable surface for the solid support;
      a protective housing for the substrate; and
   (b) a reader device, wherein the reader device is configured to detect the target antigen via interaction with the cartridge device.

3. The system of claim 2, wherein the detectable label comprises a fluorophore.

4. The system of claim 2, wherein the reader device is configured to detect the target antigen by optically interrogating the complexes in the cartridge.

5. The system of claim 4, wherein the reader device comprises:
   a light source configured to direct light toward the substrate; and
   a photodetector configured to detect light from the substrate.

6. The system of claim 4, wherein the reader device is configured to detect an optically-detectable change related to the complexes interacting with the target antigen.

7. The system of claim 6, wherein the optically-detectable change comprises a change in at least one of optical absorption, reflectivity, or fluorescence.

8. The system of claim 7, wherein the optically-detectable change is fluorescence.

9. The system of claim 2, wherein the cartridge device further comprises an antenna, and wherein the reader device is configured to detect the antigen based on data communicated via the antenna.

10. The system of claim 9, wherein the data communicated via the antenna is indicative of one or more measurements obtained by the cartridge device.

11. The system of claim 3, wherein the system is a portable, hand held device.

* * * * *